(12) United States Patent
Garcia et al.

(10) Patent No.: US 10,533,415 B2
(45) Date of Patent: Jan. 14, 2020

(54) FORMATION SAMPLING METHODS AND SYSTEMS

(71) Applicant: Schlumberger Technology Corporation, Sugar Land, TX (US)

(72) Inventors: German Garcia, Katy, TX (US); Hadrien Dumont, Houston, TX (US); Vinay K. Mishra, Katy, TX (US); Li Chen, Katy, TX (US); Abhishek Agarwal, Sugar Land, TX (US); Cosan Ayan, Clamart (FR)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 448 days.

(21) Appl. No.: 15/183,090

(22) Filed: Jun. 15, 2016

(65) Prior Publication Data
US 2017/0022809 A1    Jan. 26, 2017

Related U.S. Application Data

(60) Provisional application No. 62/175,987, filed on Jun. 15, 2015.

(51) Int. Cl.
*E21B 49/08* (2006.01)
*E21B 49/10* (2006.01)
(Continued)

(52) U.S. Cl.
CPC ............ *E21B 49/088* (2013.01); *E21B 49/10* (2013.01); *G01N 33/24* (2013.01); *G01N 21/31* (2013.01); *G01N 21/94* (2013.01)

(58) Field of Classification Search
CPC .. E21B 49/08–10; G01N 33/24; G01N 21/94; G01N 21/31
See application file for complete search history.

(56) References Cited

U.S. PATENT DOCUMENTS 7,458,419 B2 * 12/2008 Nold, III ................ E21B 49/10
166/100
8,555,968 B2    10/2013 Zazovsky et al.
(Continued)

OTHER PUBLICATIONS

Ayan et al., Characterizing Permeability with Formation Testers, Oilfield Review, pp. 2-23, Autumn 2001, Schlumberger, Sugar Land, TX USA.
(Continued)

*Primary Examiner* — George S Gray
(74) *Attorney, Agent, or Firm* — Trevor G. Grove

(57) ABSTRACT

A formation sampling method includes disposing a downhole tool comprising a packer and an expandable probe within a wellbore. The method also includes performing pressure transient testing by setting the expandable packer and the probe to engage a wall of the wellbore and measuring a pressure response at the expandable packer and the probe while withdrawing formation fluid into the downhole tool through the expandable packer. The method further includes monitoring a contamination level of the formation fluid during the pressure transient testing, and performing formation sampling with the probe in response to determining that the monitored contamination level meets a predetermined threshold.

20 Claims, 4 Drawing Sheets

(51) Int. Cl.
G01N 33/24 (2006.01)
G01N 21/31 (2006.01)
G01N 21/94 (2006.01)

(56) References Cited

U.S. PATENT DOCUMENTS

| | | | | |
|---|---|---|---|---|
| 2004/0000433 A1* | 1/2004 | Hill | ......................... | E21B 49/08 |
| | | | | 175/59 |
| 2008/0115574 A1* | 5/2008 | Meek | ...................... | E21B 17/10 |
| | | | | 73/152.03 |
| 2011/0162836 A1* | 7/2011 | Church | ................... | E21B 49/10 |
| | | | | 166/264 |
| 2016/0130940 A1 | 5/2016 | Hsu et al. | | |

OTHER PUBLICATIONS

Flores De Dios, et al., New Wireline Formation Tester Development Makes Sampling and Pressure Testing Possible in Extra-Heavy Oils in Mexico, SPE 159868, 9 pages, SPE Annual Technical Conference and Exhibition, Oct. 8-10, 2012, San Antonio, TX, USA.

* cited by examiner

FORMATION SAMPLING METHODS AND SYSTEMS

CROSS-REFERENCE TO RELATED APPLICATIONS

This application claims the benefit of, and priority to, U.S. patent Application Ser. No. 62/175,987, filed Jun. 15, 2015, which application is expressly incorporated herein by this reference in its entirety.

BACKGROUND OF THE DISCLOSURE

Wellbores (also known as boreholes) are drilled to penetrate subterranean formations for hydrocarbon prospecting and production. During drilling operations, evaluations may be performed of the subterranean formation for various purposes, such as to locate hydrocarbon-producing formations and manage the production of hydrocarbons from these formations. To conduct formation evaluations, the drill string may include one or more drilling tools that test and/or sample the surrounding formation, or the drill string may be removed from the wellbore, and a wireline tool may be deployed into the wellbore to test and/or sample the formation. These drilling tools and wireline tools, as well as other wellbore tools conveyed on coiled tubing, drill pipe, casing or other conveyers, are also referred to herein as "downhole tools."

Formation evaluation may involve drawing fluid from the formation into a downhole tool for testing and/or sampling. Various devices, such as probes and/or packers, may be extended from the downhole tool to isolate a region of the wellbore wall, and thereby establish fluid communication with the subterranean formation surrounding the wellbore. Fluid may then be drawn into the downhole tool using the probe and/or packer. Within the downhole tool, the fluid may be directed to one or more fluid analyzers and sensors that may be employed to detect properties of the fluid.

SUMMARY

The present disclosure relates to a formation sampling method that includes disposing a downhole tool that has an expandable packer and an extendable probe within a wellbore, performing pressure transient testing by setting the expandable packer and the probe to engage a wall of the wellbore and measuring a pressure response at the expandable packer and the probe while withdrawing formation fluid into the downhole tool through the expandable packer, monitoring a contamination level of the formation fluid during the pressure transient testing, and performing formation sampling with the probe in response to determining that the monitored contamination level meets a predetermined threshold.

The present disclosure also relates to a downhole tool that includes an expandable packer and an extendable probe. The expandable packer includes a drain for withdrawing a first portion of formation fluid into the downhole tool, and the extendable probe includes a sample inlet and a guard inlet for withdrawing a second portion of formation fluid into the downhole tool. The downhole tool also includes a fluid analyzer to monitor a contamination level of the first portion of the formation fluid and a controller. The controller is designed to execute instructions stored within the downhole tool to: perform pressure transient testing by setting the expandable packer and the probe to engage a wall of the wellbore and measuring a pressure response at the expandable packer and the probe while withdrawing the first portion of the formation fluid into the downhole tool through the expandable packer; and perform formation sampling with the extendable probe in response to determining that the monitored contamination level meets a predetermined threshold.

BRIEF DESCRIPTION OF THE DRAWINGS

The present disclosure is understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

It is to be understood that the present disclosure provides many different embodiments, or examples, for implementing different features of various embodiments. Specific examples of components and arrangements are described below to simplify the present disclosure. These are, of course, merely examples and are not intended to be limiting.

The present disclosure relates to methods and systems for formation sampling where the cleanup phase is accelerated by using an expandable packer for at least a portion of the cleanup phase. During formation testing and sampling, the fluid initially withdrawn into the downhole tool may be contaminated with drilling fluid, mud cake and other components. However, as formation testing and sampling continues, the levels of contaminants are reduced as fluid is drawn into the tool from deeper within the formation such that virgin formation fluid primarily enters the downhole tool. According to certain embodiments, fluid may be considered to be representative of virgin formation fluid when contamination levels are at or below a predetermined level, such as 5%, 4%, or 3%. At these levels, the properties of the fluid may closely correlate to properties of the virgin formation fluid, and therefore the sample may be representative of the virgin formation fluid. The "cleanup phase" is the period during which fluid is withdrawn into the downhole tool to reduce the contamination level to the predetermined level. According to certain embodiments, a downhole tool may include both an expandable packer and an extendable probe for withdrawing fluid into the formation. The expandable packer may be employed to withdraw relatively large amounts of fluid into the downhole tool, as compared with extendable probes, to accelerate the cleanup phase. Once an acceptable contamination level is detected, the extendable probe may be employed to withdraw substantially virgin formation fluid into the tool for testing and/or sampling.

Figure 1:
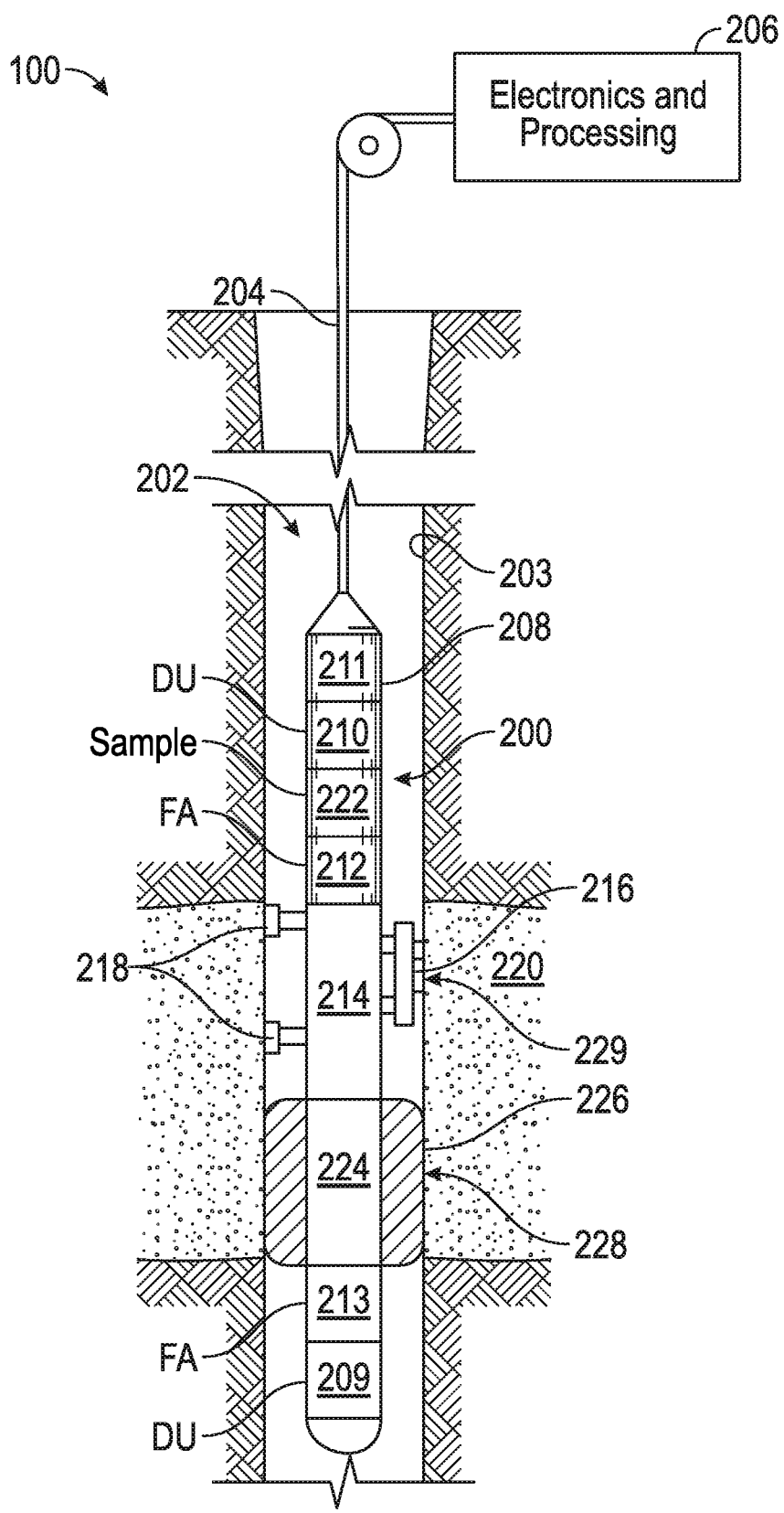
FIG. 1 is a schematic view of an embodiment of a wellsite system that may employ formation sampling systems and methods, according to aspects of the present disclosure.

FIG. 1 depicts an example of a wellsite system 100 that may employ the formation testing and sampling systems and techniques described herein. A downhole tool 200 is suspended in a wellbore 202 from the lower end of a multi-conductor cable 204 that is spooled on a winch at the surface. The cable 204 is communicatively coupled to an electronics and processing system 206. The electronics and processing systems 206 may one or more processors, volatile memory (e.g., random-access memory) and/or non-volatile memory (e.g., flash memory and a read-only memory (ROM)). Coded application instructions (e.g., software that may be executed by the processor to enable the control and analysis functionality described herein) and data may be stored in the memory. As shown in FIG. 1, the downhole 200 is conveyed on a wireline; however, in other embodiments, the downhole tool may be conveyed on a drill string, a wired drill pipe, a combination of wired drill pipe and wireline, or other suitable types of conveyance.

The downhole tool 200 includes an elongated body 208 that houses modules 209, 210, 211, 212, 213, 214, 222, and 224 that provide various functionalities including fluid sampling, fluid testing, operational control, and communication, among others. For example, the module 211 may be a power and electronics module that provides electrical power for the downhole tool 200. The modules 209 and 210 may be pump modules that direct formation fluid through the downhole tool. Further, the modules 212 and 213 may be fluid analysis modules that include optical spectrometers and other sensors that can be employed to determine properties of the formation fluid. In other embodiments additional modules may be included in the downhole tool 200 to provide further functionality such as resistivity measurements, operational control, communications, coring, and/or imaging, among others. Moreover, in certain embodiments, the relative positions and arrangement of the modules within the downhole tool 200 may vary.

As shown in FIG. 1, the module 214 is a sampling probe module 214 that has a selectively extendable probe 216 and backup pistons 218 that are arranged on opposite sides of the elongated body 208. The extendable probe 216 is configured to selectively seal off or isolate selected portions of the wall 203 of the wellbore 202 to fluidly couple to the adjacent formation 220 and to withdraw fluid samples from the formation 220. The probe 216 may include a single inlet or multiple inlets designed for guarded or focused sampling.

The downhole tool 200 also includes an expandable packer module 224 that has an expandable packer 226 that can be expanded radially outward from the downhole tool 200 to engage the wall 203 of the wellbore 202. In the expanded position, as shown in FIG. 1, the packer 226 circumferentially engages the wall 203 of the wellbore to fluidly couple to the adjacent formation 220 and to withdraw fluid samples from the formation 220. According to certain embodiments, the packer 226 extends around the entire circumference of the wellbore to seal a cross-section of the wellbore 202.

The formation fluid may be withdrawn into the tool 200 through the extendable probe 216 and/or through the expandable packer 226. Within the tool, the formation fluid may be analyzed to determine fluid properties, such as contamination levels, viscosity, fluid density, optical density, and compressibility, among others. The formation fluid may then be expelled to the wellbore through a port in the body 208 or the formation fluid may be sent to a fluid sampling module 222. The fluid sampling module may include sample chambers that store the formation fluid. In the illustrated example, the electronics and processing system 206 and/or a downhole control system are configured to control the extendable probe assembly 216 and the expandable packer 226 and may also control the formation testing and sampling methods described herein.

Figure 2:
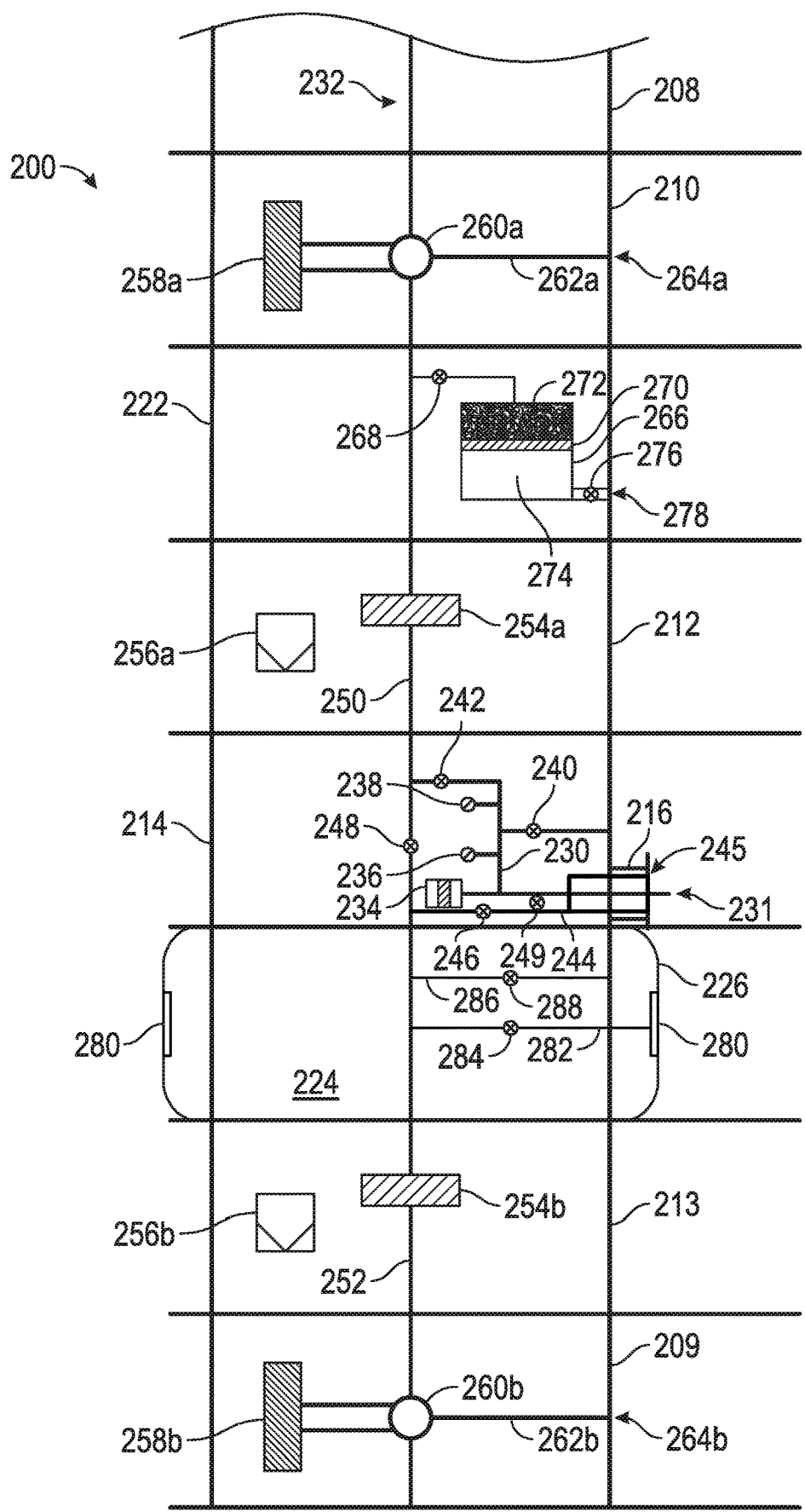
FIG. 2 is a schematic representation of an embodiment of a downhole tool for performing formation sampling, according to aspects of the present disclosure.

FIG. 2 is a schematic diagram of a portion of the downhole tool 200. The downhole tool 200 includes the probe module 214, which includes the extendable probe 216 for directing formation fluid into the downhole tool 200. The probe module 214 includes a sample flowline 230 that directs the formation fluid from a sample inlet 231 to a main flowline 232 that extends through the downhole tool 200. The probe module 214 also includes a pretest pump 234 and pressure gauges 236 and 238 that may be employed to conduct formation pressure tests. An equalization valve 240 may be opened to expose the flowline 230 to the pressure in the wellbore, which in turn may equalize the pressure within the downhole tool 200. Further, an isolation valve 242 may be closed to isolate the formation fluid within the sample flowline 230 and/or to isolate the sample flowline 230 from the main flowline 232. The isolation valve 242 may be opened to direct the formation fluid from the sample flowline 230 to the main flowline 232.

The probe module 214 also includes a guard flowline 244 that directs the formation fluid from a guard inlet 245 to the main flowline 232. According to certain embodiments, the guard inlet 245 may be disposed circumferentially around the sample inlet 231 to provide focused sampling. During sampling, the more contaminated formation fluid may flow through the guard inlet 245 and the less contaminated formation fluid may flow through the sample inlet 231. An isolation valve 246 may be closed to isolate the formation fluid within the guard flowline 244 and/or to isolate the guard flowline 244 from the main flowline 232. The isolation valve 246 may be opened to direct the formation fluid from the guard flowline 244 to the main flowline 232. A valve 249 may be disposed between the sample flowline 230 and the guard flowline 244. The valve 249 may be opened to allow the fluid from the flowlines 230 and 244 to mix, for example, during an initial cleanup phase where formation fluid entering the downhole tool 200 is directed through the tool and returned to the wellbore. Once an acceptable contamination level is reached, the valve 249 may be closed to isolate the fluid within the sample flowline 230 from the fluid within the guard flowline 244.

A valve 248 also may be disposed in the main flowline 232 to isolate a first portion 250 of the main flowline 232 (e.g., above the valve 248) from a second portion 252 of the main flowline (e.g., below the valve 248). During sampling, the valve 248 may be closed and formation fluid from the sample flowline 230 may be directed through the first portion 250 of the main flowline 232 to the fluid analysis module 212 and the sample module 222, while formation fluid from the guard flowline 244 is directed through the second portion 252 of the main flowline 232 to the fluid analysis module 254 and the pump module 209.

The first portion 250 of the main flowline 232 directs the formation fluid through the downhole tool 200 to the fluid analysis module 212 and the second portion 252 directs the formation fluid through the downhole tool 200 to the fluid analysis module 213. Each fluid analysis module 212 and 213 includes a fluid analyzer 254a or 254b that can be employed to provide downhole fluid measurements. For example, the fluid analyzers 254a and 254b may include an optical spectrometer and/or a gas analyzer designed to measure properties such as, optical density, fluid fluorescence, fluid composition, and the fluid gas oil ratio (GOR), among others. One or more additional measurement devices, such as temperature sensors, pressure sensors, viscosity sensors, resistivity sensors, chemical sensors (e.g., for measuring pH or $H_2S$ levels), and gas chromatographs, also may be included within the fluid analyzers 254a and 254b.

In certain embodiments, the fluid analysis modules 212 and 213 may include a controller 256a or 256b such as a microprocessor or control circuitry, designed to calculate certain fluid properties based on the sensor measurements. The controllers 256a and 256b may include memory that stores coded application instructions (e.g., software that may be executed by the controller to enable the control and analysis functionality described herein) and data 130 (e.g., acquired measurements and/or the results of processing). For example, the controllers 256a and 256b may calculate contamination levels of the formation fluid withdrawn into the tool through the sample flowline 230 and the guard flowline 244. Further, in certain embodiments, the controllers 256a and 256b may govern sampling operations based on the fluid measurements or properties. Moreover, in other embodiments, the controllers 256a and 256b may be disposed within another module of the downhole tool 200, or may be combined into a single downhole controller.

The downhole tool 200 also includes the pump modules 209 and 210. Each pump module 209 and 210 includes a pump 258a or 258b designed to provide motive force to direct the fluid through the downhole tool 200. According to certain embodiments, the pumps 258a and 258b may be hydraulic displacement units that receive fluid into alternating pump chambers. A valve block 260a or 260b may direct the fluid into and out of the alternating pump chambers. The valve blocks 260a and 260b also may direct the fluid exiting the pump 258a and 258b through the main flowline 232 or may divert the fluid to the wellbore through flowlines 262a and 262b connected to ports 264a and 264b in the body 208 of the downhole tool 200. Further, in certain embodiments, the valve blocks 260a and 260b may direct fluid from the wellbore into the downhole tool 200 through the ports 264a and 264b.

The downhole tool 200 also includes one or more sample modules 222 designed to store samples of the formation fluid within a sample chamber 266. As shown in FIG. 2, a single sample chamber 266 is included within the sample module 222. However, in other embodiments, multiple sample chambers may be included within the sample module 222 to provide for storage of multiple formation fluid samples. Further, in other embodiments, multiple sample modules 222 may be included within the downhole tool 200. Moreover, other types of sample chambers, such as single phase sample bottles, among others, may be employed in the sample module 222.

The sample module 222 includes a valve 268 that may be actuated to divert the formation fluid into the sample chamber 266. The sample chamber 266 includes a floating piston 270 that divides the sample chamber into two volumes 272 and 274. As the formation fluid flows through the main flowline 232, the valve 268 may be actuated to divert the formation fluid into the volume 272. In certain embodiments, the pump 258a or 258b may provide the motive force to direct the fluid through the main flowline 232 and into the sample chamber 266. The formation fluid may be stored within the volume 272 and, in certain embodiments, may be brought to the surface for further analysis. The sample module 222 also may include a valve 276 that can be opened to expose the volume 274 of the sample chamber 266 to the annular pressure through a port 278 in the body 208 of the downhole tool 200. In certain embodiments, the valve 276 may be opened to allow buffer fluid to exit the volume 274 to the wellbore, which may provide backpressure during filling of the volume 272 that receives formation fluid. In other embodiments, the volume 274 may be filled with a low pressure gas that provides backpressure during filling of the volume 272.

The downhole tool 200 also includes the packer module 224. According to certain embodiments, the packer module 224 may be disposed directly adjacent to the probe module 214. The adjacent and close spacing between the packer module 224 and the probe module 214 may enable both the packer 226 and the probe 216 to be employed to sample from a similar part of the formation 220. For example, as shown in FIG. 1, the packer 228 may engage the wellbore wall 203 at a first location 228 within the wellbore, and the probe 216 may engage the wellbore wall 203 at a second location 229 within the wellbore. The locations 228 and 229 may be relatively close to one another, for example, within approximately 10 or fewer feet of one another, or more specifically, within approximately 4 feet of one another.

The packer module includes the packer 226 that may be expanded to contact the wellbore wall. The packer 226 includes drains 280 that may be disposed against the wellbore wall when the packer 226 is in the expanded position. According to certain embodiments, the drains 280 may be spaced circumferentially around the packer 226. Formation fluid may be withdrawn into the downhole tool 200 through the drains 280 and directed through a sample flowline 282 to the main flowline 232. The pump 260a or 260b may provide the motive force for withdrawing formation fluid into the downhole tool through the drains 280. The formation fluid may then be directed through the second portion 252 of the main flowline and the first portion 250 of the main flowline 232 to the sample chamber 266. Further, in certain embodiments, the formation fluid may be directed through the main flowline 232 to one or both ports 264a and 264b to be returned to the wellbore. A valve 284 may be disposed in the sample flowline 282 and may be closed to isolate the sample flowline 282 from the main flowline 232. The valve 284 may be opened to direct formation fluid from the drains 280 through the sample flowline 282 to the main flowline 232.

The packer module 224 also includes an inflation flowline 286 that may be employed to inflate the packer 226. A valve 288 may be disposed in the inflation flowline 286 and may be opened to enable fluid to flow through the inflation flowline 286 to inflate the packer 226. According to certain embodiments, fluid from the wellbore may be pumped into the downhole tool 200 through a port 264a or 264b by pump 258a or 258b. The fluid may be directed through the main flowline 272 and into the inflation flowline 286 to inflate the packer 226. The valve 288 may then be closed to maintain the packer 226 in the inflated position, for example during formation testing sampling. In certain embodiments, the inflation flowline 286 also may be employed to deflate the packer 226. For example, the valve 288 may be opened and pump 258a or 258b may be employed to direct fluid from the packer 226, through the flowline 286 and main flowline 272 to exit the downhole tool 200 through the port 264a or 260b.

Figure 3:
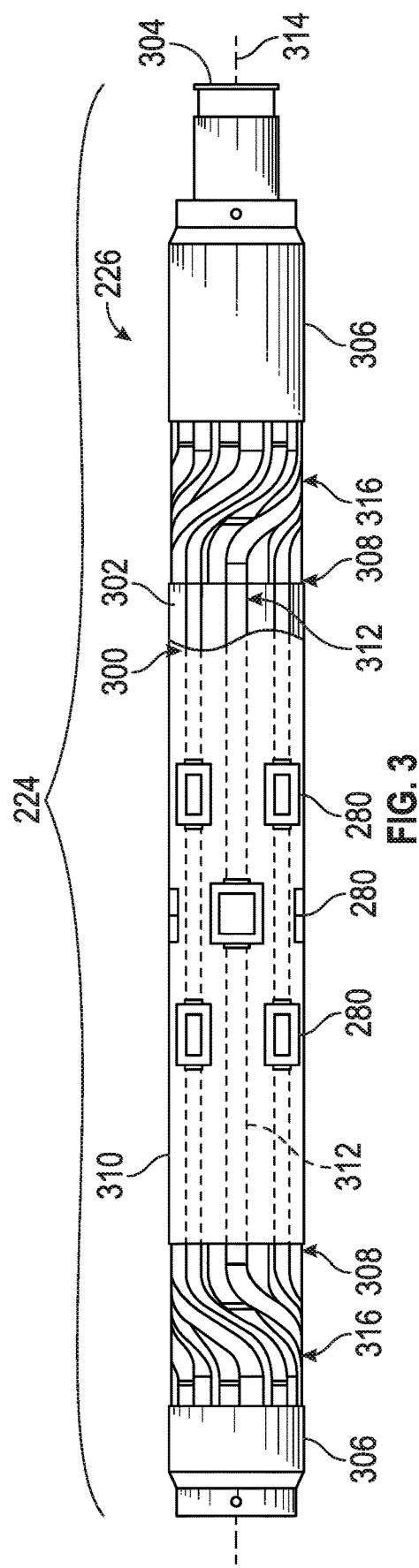
FIG. 3 is a schematic representation of an embodiment of the expandable packer shown in FIG. 2, according to aspects of the present disclosure.

FIG. 3 depicts an embodiment of the packer module 224. The packer 226 includes an outer structural layer 300 that is expandable in a wellbore to form a seal with the surrounding wellbore wall or casing. Disposed within an interior of the outer structural layer 300 is an inner, inflatable bladder 302 disposed within an interior of the outer structural layer 300. For ease of illustration, FIG. 3 depicts the packer 226 with a portion of the outer structural layer 300 cut away to show the internal components of the outer structural layer 300 and the inflatable bladder 302. The inflatable bladder 302 can be formed in several configurations and with a variety of materials, such as a rubber layer having internal cables. In one example, the inflatable bladder 302 is selectively expanded by fluid delivered via an inner mandrel 304. According to certain embodiments, fluid may be delivered within the inner mandrel 304 via the inflation flowline 286, as described above with respect to FIG. 2. The packer 226 also includes a pair of mechanical fittings 306 that are mounted around the inner mandrel 304 and engaged with axial ends 308 of the outer structural layer 300.

The outer structural layer 300 includes the drains 280 through which fluid may be drawn into the packer 226 from the subterranean formation. Further, in certain embodiments, fluid also may be directed out of the packer 226 through the drains 280. The drains 280 may be embedded radially into a sealing element or seal layer 310 of the outer structural layer 300. By way of example, the seal layer 310 may be cylindrical and formed of an elastomeric material selected for hydrocarbon based applications, such as a rubber material. As shown in FIG. 3, tubes 312 may be operatively coupled to the drains 280 for directing the fluid in an axial direction to one or both of the mechanical fittings 306. The tubes 312 may be aligned generally parallel with a packer axis 314 that extends through the axial ends of outer structural layer 300. The tubes 312 may be at least partially embedded in the material of sealing element 310 and thus may move radially outward and radially inward during expansion and contraction of outer layer 300.

The tubes 312 are coupled to moveable members 316 that direct fluid from the tubes 312 to the interior of the mechanical fittings 18, where the fluid is directed to the main flowline 232 (FIG. 2). By way of example, each movable member 316 may be pivotably coupled to its corresponding mechanical fitting 306 for pivotable movement about an axis generally parallel with packer axis 314. In the illustrated embodiment, multiple movable members 316 are pivotably mounted to each mechanical fitting 306. The movable members 316 are designed as flow members that allow fluid flow between the tubes 312 and an interior of the mechanical fittings 306. In particular, certain movable members 316 are coupled to certain tubes 312 extending to the drains 280, allowing fluid from the drains 280 to be routed to the interior of the mechanical fittings 306, which may direct the fluid to the sample flowline 282 (FIG. 2). Further, in certain embodiments, the movable members 316 also may direct fluid from the interior of the mechanical fittings 306 to the tubes 312 to be expelled from the packer 226 through the drains 280. The movable members 316 are generally S-shaped and designed for pivotable connection with both the mechanical fitting 306 and the corresponding tubes 312. As a result, the movable members 316 can be pivoted to allow the packer 226 to expand and contract.

Figure 4:
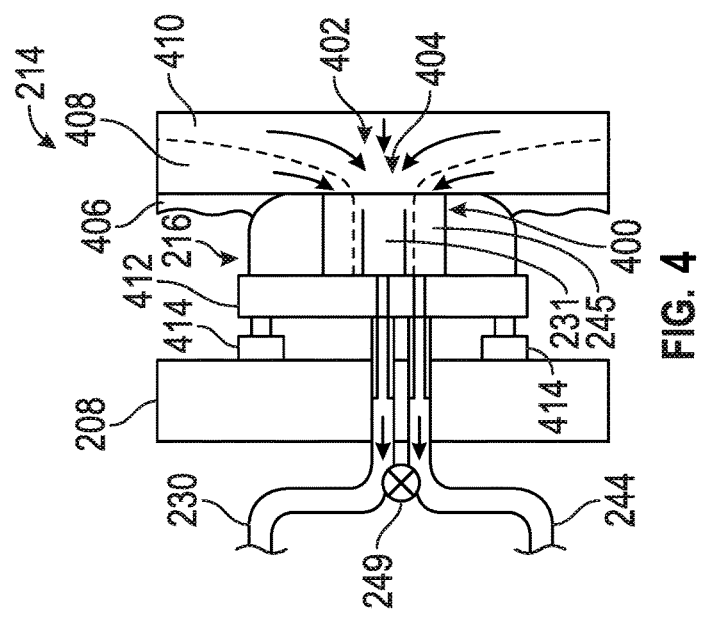
FIG. 4 is a schematic representation of an embodiment of the extendable probe shown in FIG. 2, according to aspects of the present disclosure.

FIG. 4 depicts an embodiment of the probe module 214. During a sampling operation, an intake 400 of the probe 216 may be extended into engagement with the wellbore wall 203 (FIG. 1). According to certain embodiments, the intake 400 may be constructed of an elastomeric material and may be mounted on a plate 412 coupled to pistons 414. The pistons 414 may be actuated to extend the plate 412 and intake 400 away from the body 208 of the downhole tool 200 to place the intake 400 into engagement with the wall 203 of the wellbore 202.

The intake 400 includes the sample inlet 231 and the guard inlet 245. The sample inlet 231 is disposed in a central region of the intake 400, and the guard inlet 245 is disposed in the annular region surrounding the sample inlet 231. During operation, formation fluid 402 may be drawn from a sampling zone 404 (e.g., at the wall 203 of the wellbore 202) into the intake 400. The formation fluid 402 near the center of the sampling zone 404 may be drawn into the sample inlet 231, and the formation fluid 402 near the outside edge of the intake 400 and sampling zone 404 may be drawn into the guard inlet 245. In an example sampling operation, debris of mud cake 406 on or at the wall 203 may be initially drawn into the intake 400. As pumping continues, the filtrate fluid 408 adjacent to the wall 203 may be drawn into the intake 400. The debris and the filtrate fluid may be drawn into the intake 400 during the cleanup phase of formation sampling. As pumping further continues, the virgin formation fluid 410 adjacent to and behind the filtrate fluid 408 may be drawn into the intake 400.

The sample inlet 231 directs formation fluid to the sample line 230, and the guard inlet 245 directs formation fluid to the guard line 244. As described above with respect to FIG. 2, the fluid analyzers 254a and 254b may determine properties of the formation fluid including the contamination levels. When the contamination level falls below an acceptable level, formation fluid may be directed through the sample flowline 230 to a sample chamber 266.

Figure 5:
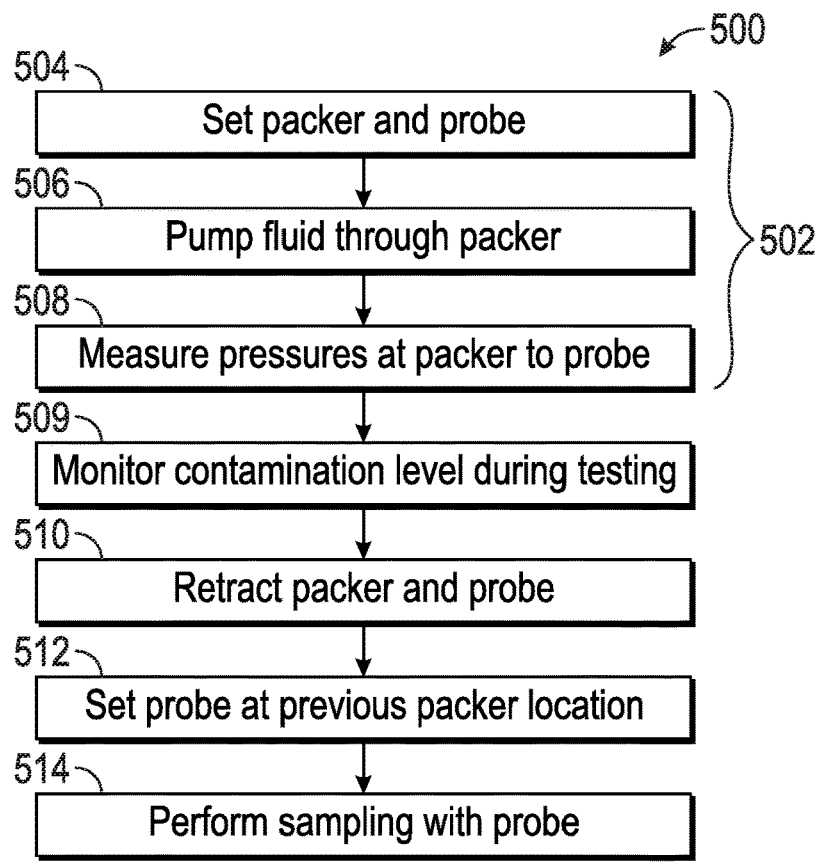
FIG. 5 is a flowchart depicting a formation sampling method, according to aspects of the present disclosure.
Figure 6:
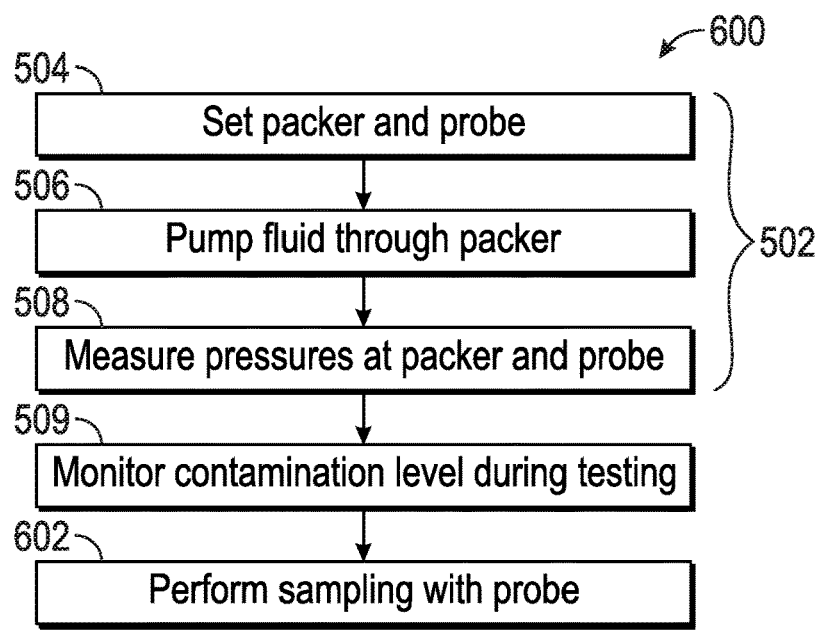
FIG. 6 is flowchart depicting another formation sampling method, according to aspects of the present disclosure.

FIGS. 5 and 6 are flowcharts depicting methods 500 and 600 that may be employed to perform formation sampling while using the packer 226 to accelerate the cleanup phase. According to certain embodiments, the methods may be executed, in whole or in part, by the controllers 256a and 256b. For example, the controllers 256a and 256b may execute code stored within circuitry of the controllers 256a and 256b, or within a separate memory or other tangible readable medium, to perform the methods 500 and 600. Further, in certain embodiments, the controllers 256a and 256b may operate in conjunction with a surface controller, such as the electronics and processing system 206 (FIG. 1), which may perform one or more operations of the methods 500 and 600.

Referring to FIG. 5, the method 500 may begin by performing pressure transient testing (block 502). According to certain embodiments, the pressure testing may determine vertical and/or horizontal permeability and may include a vertical interference test (VIT) or an interval pressure-transient test (IPTT), or both. The pressure testing may begin by setting (block 504) the packer 226 and the probe 216. For example, the downhole tool 200 may be conveyed to a desired location within the wellbore 202 and the probe 216 may be extended to engage the wall 203 of the wellbore 202. The packer 226 also may be expanded, for example, by directing wellbore fluid into the packer 226 though the inflation flowline 286. Pretests may also be performed at the packer 226 and the probe 216, as described further below to verify sealing with the wellbore wall 203.

In certain embodiments, the packer 226 and the probe 216 may be set simultaneously; however in other embodiments, the packer 226 and the probe 216 may be set (block 504) sequentially, with either the packer 226 or the probe 216 being set first. In one embodiment, the packer 226 may be set first and a pretest may be performed for the packer 226 by closing isolation valve 248, opening valve 284, and operating the pump 258b to draw formation fluid into the downhole tool 200 through the drains 280 and sample flowline 282. The formation fluid may then be expelled to the wellbore through the port 264b. During the packer pretest (e.g., while pumping formation fluid through the sample flowline 282), the probe 216 may be set by extending the probe 216 to the wellbore wall 203 and performing a pretest at the probe 216. For example, to perform the probe pretest, the valves 242 and 246 may be closed and the pump 234 may be operated to withdraw formation fluid into the downhole tool 200 through the inlets 245 and 231.

During the pretests, pressures may be monitored to determine when the pressures within the flowlines reaches formation pressure. For example, pressure gauges 236 and/or 238 may be employed to monitor the pressure during the probe pretest, while a pressure gauge within the fluid analyzer 254b may be employed to monitor the pressure during the packer pretest. Once formation pressures are detected at both the packer 226 and the probe 216, the pretests may be complete.

In response to detecting completion of the pretests, the controllers 256a, 256b, and/or 206 may set the downhole tool 200 to begin pumping (block 506) solely through the packer 226. For example, operation of the pretest pump 234 may cease and valve 248 may be openend. Valves 242 and 246 may be closed to isolate the probe 216 from the main flowline 232, while the valve 284 remains open to allow fluid to enter the downhole tool 200 through the packer 226. One or both pumps 258a and 258b may then be operated to withdraw fluid into the packer 226 through the drains 280 and the sample flowline 282.

During withdrawal of fluid into the packer 226, the pressure may be measured (508) at the packer 226 and the probe 216. For example, pressure gauges 236 and/or 238 may be employed to measure the pressure response at the probe 216. Note that because valves 242 and 246 and closed and pump 234 is not operating, no fluid is withdrawn into the probe 216. However, the formation pressure response can be measured at the probe 216 because the flowlines 230 and 244 are exposed to the formation. Pressures may also be measured at the packer 226, for example, using pressure sensors within the fluid analyzers 254a and 254b. Further, in other embodiments pressure sensors may be coupled to the drains 280 to measure pressures detected at the individual drains 280. One or more drains 280 of the packer 226 may operate as sink port and the probe 216 may operate as an observation port. Further, in certain embodiments, other drains 280 of the packer 226 may also function as observation ports. The pressure measurements from the packer 226 and the probe 216 can be employed for pressure transient analysis to determine horizontal and/or vertical permeabilities and anisotropies.

During the pressure transient testing (block 502), the contamination level of the formation fluid may also be monitored (block 509). For example, during withdrawal of fluid into the packer 226, properties of the formation fluid flowing through the downhole tool may be measured to determine when the contamination level meets a predetermined threshold. For example, the fluid analyzers 254a and 254b may measure fluid properties, such as optical densities and compositions, to determine the contamination level. Further, in certain embodiments, other properties such as viscosity, compressibility, resistivity, fluid density, among others may be employed to determine when an acceptable contamination level is reached. A more detailed description of contamination monitoring can be found in commonly assigned U.S. Pat. No. 8,555,968 to Zazovsky et al., which is hereby incorporated by reference herein in its entirety for all purposes.

In response to determining that the contamination level is at or below a desired level, pumping may cease and the packer 226 and probe 216 may be retracted (block 510). For example, as shown in FIG. 2, the inflation fluid may exit the packer 226 through the flowline 286 to retract the packer 226. In certain embodiments, mechanical springs also may be employed to retract the packer 226. For the probe 216 as shown in FIG. 3, the pistons 414 (FIG. 4) may be employed to retract the intake 400 away from the wellbore wall 203 and towards the body 208 of the downhole tool 200. The tool may then be moved within the wellbore 202 to set the probe 216 at the previous location of the packer 226 (block 512). For example, as shown in FIG. 1, the cable 204 may be employed to convey the downhole tool 200 further within the wellbore 202 so that the probe 216 is disposed at the previous packer location 228. In other embodiments, the probe module 214 may be disposed on the downhole tool 200 below the packer module 224, and in these embodiments, the downhole tool 200 may be retracted within the wellbore 202 to place the probe 216 at the previous packer location. In further embodiments, the probe 216 may be set in the vicinity (e.g., within 1 foot, 2 feet, 3 feet, or 4 feet) of the previous location of the packer 228. By disposing the probe 216 at the previous packer location 228, the probe 216 takes advantage of the cleanup provided by the packer 226. However, in certain situations, the probe 216 may be able to obtain a better seal with the mudcake in the vicinity of the previous location of the packer 228, but not at the previous location of the packer 228 where the mudcake may have been affected by the packer 226. By disposing the probe 216 in the vicinity of the previous location of the packer 228, the probe 216 still 216 takes advantage of the cleanup provided by the packer 226.

Once the probe 216 is disposed at the previous packer location 228 or in the vicinity of the previous packer location 228, the probe 216 may be extended to engage the wellbore wall 203. Formation sampling may then be performed (block 514) using the probe 216. For example, as shown in FIG. 2, the probe 216 may be operated in a "split-flow" configuration where the sample flow line 230 is isolated from the guard flowline 244 to allow for focused sampling. In particular, valves 242 and 246 may be opened and pumps 258a and 258b may be operated to direct formation fluid into the downhole tool 200 through the sample inlet 231 and the guard inlet 245. The valves 248 and 249 may be closed so that the formation fluid flowing through the sample flowline 230 remains isolated from the formation fluid flowing through the guard flowline 244. As noted above with respect to FIG. 3, the sampling flowline 230 may effectively capture the formation fluid 402 concentrated in the central area of the intake 400. The formation fluid 402 concentrated in the central area of the intake 400 may primarily include the virgin formation fluid 410, and the formation fluid 402 concentrated around the perimeter of the intake 400 may include the mudcake 406, the filtrate fluid 408, and/or the virgin formation fluid 410. Thus, the separation of the sample flowline 230 and the guard flowline 244, allows for a portion of the formation fluid that contains primarily virgin formation fluid 410 to be separated from the remaining formation fluid that may be contaminated with mudcake 406 and filtrate fluid 408.

The formation fluid flowing through the guard flowline 244 may be directed through the second portion 252 of the main flowline 232 and through the fluid anlayzer 254b, while the formation fluid flowing through the sample flowline 230 may be directed through the first portion 250 of the main flowline 232 and through the fluid anlayzer 254a. The contamination levels, as well as other properties, may be measured and monitored by the fluid analyzers 254a and 254b. During this measurement and monitoring phase, the formation fluid may be expelled to the wellbore through the ports 264a and 264b. When the fluid analyzer 254a determines that the formation fluid flowing through the sample flowline 230 has a contamination level below a desired level, the formation fluid properties measured by the fluid analyzer 254a during this time may be representative of properties of the virgin formation fluid. In certain embodiments, valve 268 may also be opened and a portion of the formation fluid may be directed into the sample chamber 266 for storage and further analysis at the surface.

The method 500 described above allows a majority of the cleanup phase to be performed using the packer 226 while performing pressure testing (block 502). Accordingly, the pumping time for performing sampling (block 514) may be reduced because contamination levels may reach a desired level more quickly because a large portion of the contaminated formation fluid may be removed by the packer 226 during the pressure transient testing.

FIG. 6 depicts another method 600 for performing formation sampling while using the packer 226 to accelerate the cleanup phase. The method may begin by performing pressure testing (block 502) as described above with respect to FIG. 5. As described in detailed above, the pressure testing may include setting (block 504) the packer 226 and the probe 216; pumping (block 506) fluid through the packer 226; measuring (block 508) pressures at the packer 226 and the probe 216; and monitoring (block 509) a contamination level of the formation fluid during the pressure testing. However, rather than retracting (block 510) the packer and the probe when the contamination level meets a predetermined level, the method 600 may continue by performing (block 602) sampling when the contamination level meets a predetermined level.

As shown in FIG. 6, sampling may be performed (block 602) without moving the downhole tool 200 to another location and without retracting the packer 226 and the probe 216. For example, in response to determining that the contamination level meets a predetermined level, the controllers 256a, 256b, and/or 206 may stop operation of the pumps 258a and 258b. The valve 284 in the packer module 224 may be closed to isolate the packer flowline 282 from the main flowline 232.

Sampling may then be performed (block 602) by operating the probe 216 in the "split-flow" configuration where the sample flow line 230 is isolated from the guard flowline 244 to allow for focused sampling. In particular, valves 242 and 246 may be opened and pumps 258a and 258b may be operated to direct formation fluid into the downhole tool 200 through the sample inlet 231 and the guard inlet 245. The valves 248 and 249 may be closed so that the formation fluid flowing through the sample flowline 230 remains isolated from the formation fluid flowing through the guard flowline 244 to perform focused sampling as described in detail with respect to FIG. 5, block 514.

In another embodiment, rather than first stopping operation of the pumps 258a and 258b, sampling may be performed (block 602) by opening the valve 242 while the pumps 258a and 258b continue pumping. In this embodiment, formation fluid from both the guard inlet 245 and the packer drains 280 may flow through the second portion 252 of the main flowline 232 and commingle. The pumps 258a and 258b may then be reduced in speed and the valve 284 may be closed to isolate the packer flowline 282 from the main flowline 232. After closing the valve 284 in the packer module, the valve 248 in the probe module 214 may be closed to enable the "split flow" configuration. The valve also 249 may be closed so that the formation fluid flowing through the sample flowline 230 remains isolated from the formation fluid flowing through the guard flowline 244 to perform focused sampling as described in detail with respect to FIG. 5, block 514.

The method 600 describe above also allows a majority of the cleanup phase to be performed using the packer 226 while performing pressure testing (block 502). Accordingly, the pumping time for performing sampling (block 514) may be reduced because contamination levels may reach a desired level more quickly because a large portion of the contaminated formation fluid may be removed by the packer 226 during the pressure transient testing. Further, in the method 600, formation fluid may be sampled from the formation 220 without moving the downhole tool 200 after the pressure testing and prior to performing sampling. Because the probe module 214 and the packer module 224 are disposed in close proximity to each other on the downhole tool 200, the packer 226 and the probe 216 may be employed to withdraw formation fluid from substantially the same portion of the formation without moving the downhole tool 200.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A formation sampling method comprising:
   disposing a downhole tool comprising an expandable packer and an extendable probe within a wellbore, wherein;
   the expandable packer is configured to expand radially outward from a body of the downhole tool and engage a first region along a wall of the wellbore when the downhole tool is disposed at a first location within the wellbore;
   the extendable probe is configured to extend radially outward from the body of the downhole tool and engage a second region along the wall of the wellbore when the downhole tool is disposed at the first location: and
   the first region is longitudinally offset from the second region, without longitudinal overlap of said first and second regions; and
   performing pressure transient testing by setting the expandable packer to engage the first region along the wall of the wellbore and the extendable probe to engage the second region along the wall of the wellbore and measuring a pressure response at the expandable packer and the extendable probe while withdrawing formation fluid into the downhole tool through the expandable packer;
   monitoring a contamination level of the formation fluid during the pressure transient testing; and
   performing formation sampling with the extendable probe in response to determining that the monitored contamination level meets a predetermined threshold.

2. The formation sampling method of claim 1, wherein performing pressure transient testing comprises pumping the formation fluid into the downhole tool through the expandable packer and isolating the extendable probe from a main flowline of the downhole tool.

3. The formation sampling method of claim 2, wherein monitoring contamination levels comprises withdrawing the formation fluid into the downhole tool through one or more inlets of the expandable packer and directing the formation fluid to a fluid analyzer of the downhole tool.

4. The formation sampling method of claim 3, wherein monitoring the contamination level comprises determining optical properties of the formation fluid within the fluid analyzer.

5. The formation sampling method of claim 1, wherein performing formation sampling comprises withdrawing the formation fluid into the extendable probe through a sample inlet and a guard inlet.

6. The formation sampling method of claim 5, wherein performing formation sampling comprises directing the formation fluid from the sample inlet to a sample chamber of the downhole tool.

7. The formation sampling method of claim 1, wherein performing formation sampling comprises withdrawing formation fluid into the extendable probe while the extendable probe remains in the same position that the extendable probe was in during the pressure transient testing.

8. The formation sampling method of claim 1, comprising retracting the expandable packer from a first position within the first region and retracting the extendable probe from a second position within the second region in response to determining that the monitored contamination level meets the predetermined threshold.

9. The formation sampling method of claim 8, moving the downhole tool within the wellbore to dispose the extendable probe at the first position within the first region along the wall of the wellbore and performing the formation sampling when the extendable probe is at the first position.

10. A downhole tool comprising:
an expandable packer comprising a drain for withdrawing a first portion of formation fluid into the downhole took wherein the expandable packer is configured to expand radially outward from a body of the downhole tool and engage a first region along a wall of a wellbore when the downhole tool is disposed at a first location within the wellbore:
an extendable probe comprising a sample inlet and a guard inlet for withdrawing a second portion of formation fluid into the downhole tool, wherein the extendable probe is configured to extend radially outward from the body of the downhole tool and engage a second region along the wall of the wellbore when the downhole tool is disposed at the first location, and wherein the first region is longitudinally offset from the second region, without longitudinal overlap of said first and second regions;
a fluid analyzer to monitor a contamination level of the first portion of the formation fluid;
a controller configured to execute instructions stored within a tangible, non-transitory computer readable medium, the instructions comprising:
perform pressure transient testing by setting the expandable packer to engage the first region along the wall of the wellbore and the extendable probe to engage the second region along the wall of the wellbore and measuring a pressure response at the expandable packer and the extendable probe while withdrawing the first portion of the formation fluid into the downhole tool through the expandable packer; and
perform formation sampling with the extendable probe in response to determining that the monitored contamination level meets a predetermined threshold.

11. The downhole tool of claim 10, comprising a second fluid analyzer to monitor a contamination level of the second portion of the formation fluid.

12. The downhole tool of claim 10, comprising a first pump to direct the first portion of formation fluid through the downhole tool and a second pump to direct the second portion of formation fluid through the downhole tool.

13. The downhole tool of claim 10, comprising:
a packer module housing the expandable packer; and
a probe module housing the extendable probe, wherein the probe module is disposed in the downhole tool adjacent to the packer module.

14. The downhole tool of claim 10, wherein the fluid analyzer comprises an optical spectrometer.

15. The downhole tool of claim 10, wherein the drain comprises a plurality of drains spaced radially around a circumference of the expandable packer.

16. A formation sampling method comprising:
disposing a downhole tool comprising an expandable packer and an extendable probe within a wellbore, wherein the expandable packer is longitudinally offset from the extendable probe;
performing pressure transient testing by setting the expandable packer and the extendable probe to engage a region along a wall of the wellbore and measuring a pressure response at the expandable packer and the extendable probe while withdrawing formation fluid into the downhole tool through the expandable packer;
monitoring a contamination level of the formation fluid during the pressure transient testing;
performing formation sampling with the extendable probe in response to determining that the monitored contamination level meets a predetermined threshold;
retracting the expandable packer from a first position within the region and the extendable probe from a second position within the region in response to determining that the monitored contamination level meets the predetermined threshold; and
after retracting the expandable packer and the extendable probe, moving the downhole tool within the wellbore to dispose the extendable probe at the first position in the wellbore and performing the formation sampling when the extendable probe is at the first position.

17. The formation sampling method of claim 16, wherein performing formation sampling comprises withdrawing formation fluid into the extendable probe while the extendable probe remains in the first region that the extendable probe was in during the pressure transient testing.

18. The formation sampling method of claim 16, wherein performing pressure transient testing comprises pumping the formation fluid into the downhole tool through the expandable packer and isolating the extendable probe from a main flowline of the downhole tool.

19. The formation sampling method of claim 16, wherein performing formation sampling comprises withdrawing the formation fluid into the extendable probe through a sample inlet and a guard inlet.

20. The formation sampling method of claim 19, wherein performing formation sampling comprises directing the formation fluid from the sample inlet to a sample chamber of the downhole tool.

* * * * *